United States Patent [19]

Bartz

[11] 4,441,272
[45] Apr. 10, 1984

[54] METHOD AND APPARATUS FOR ATTRACTING USEFUL INSECTS

[76] Inventor: Gisela Bartz, Winnekendonker Str. 43, 4179 Kevelaer 2, Fed. Rep. of Germany

[21] Appl. No.: 329,613

[22] Filed: Dec. 10, 1981

Related U.S. Application Data

[63] Continuation of Ser. No. 142,683, Apr. 22, 1980, abandoned.

[30] Foreign Application Priority Data

May 10, 1979 [DE] Fed. Rep. of Germany ....... 2918852

[51] Int. Cl.³ ............................................. A01M 1/00
[52] U.S. Cl. .......................................... 43/1; 43/131; 119/23
[58] Field of Search ................. 43/131, 1; 119/23; D30/3

[56] References Cited

U.S. PATENT DOCUMENTS

| | | | |
|---|---|---|---|
| 663,728 | 12/1900 | Church | 43/114 |
| 1,980,754 | 11/1934 | Henning et al. | 43/132.1 |
| 2,000,193 | 5/1935 | Schroder | 43/121 |
| 2,077,208 | 4/1937 | Brady | 119/23 |
| 2,086,046 | 7/1937 | Preston | 43/107 X |
| 2,867,055 | 1/1959 | Lebiedzinski | 119/1 X |
| 3,115,865 | 12/1963 | Parkes et al. | 119/23 X |
| 3,803,753 | 4/1974 | Feigin et al. | 43/131 |

FOREIGN PATENT DOCUMENTS

| | | | |
|---|---|---|---|
| 222822 | 6/1910 | Fed. Rep. of Germany | 43/107 |
| 79286 | 11/1918 | Switzerland | 43/107 |

Primary Examiner—Nicholas P. Godici
Assistant Examiner—Charles L. Willis
Attorney, Agent, or Firm—Shlesinger, Arkwright, Garvey & Fado

[57] ABSTRACT

A device for attracting beneficial and useful insects comprising a container having a plurality of openings therein through which the insects may freely enter and exit, and a natural material at least partially filling the container, the natural material being cotton, rush, straw, or the like, and generating an environment preferred by the insects.

9 Claims, 1 Drawing Figure

U.S. Patent          Apr. 10, 1984          4,441,272
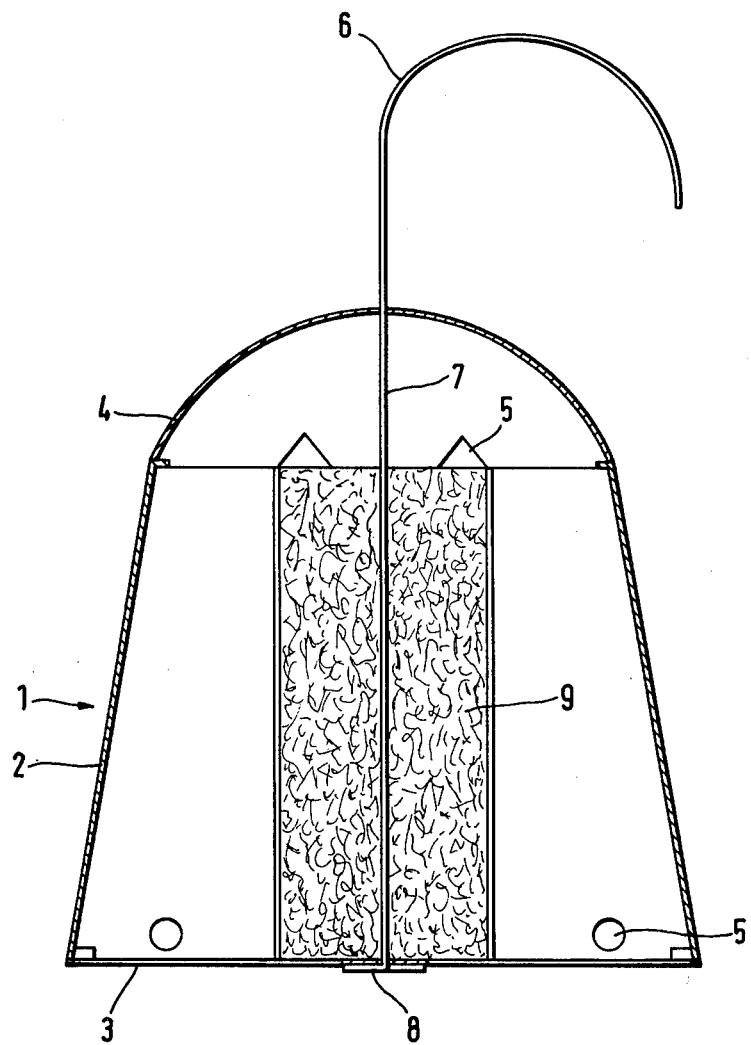

METHOD AND APPARATUS FOR ATTRACTING USEFUL INSECTS

This application is a continuation of application Ser. No. 142,683, filed Apr. 22, 1980 abandoned.

The invention relates to a device for attracting beneficial insects.

Mostly it is insecticides which are used against pets in the garden, in agriculture or forests, and with which the beneficial plants are sprayed. Trees are provided with rings of adhesives to protect them against attack by destructive insects. This manner of fighting pests is expensive in money and labor.

On the other hand, beneficial insects are known, which feed on the pests. For instance beneficial insects of the FORFICULA AURI (earwig) can consume large amounts of pests and thereby protect a culture of plants from attack by the pests. The said insects preferably consume, for example, plant-lice and fruit worms.

It is the object of the invention to make use of beneficial insects for pest control.

This problem is solved by a device for attracting beneficial insects which is characterized by a container which is filled at least in part with natural substances and which comprises several passage holes for insects.

Such devices can be set up in beds, planted terrains and the like in varying numbers, they may also be suspended. They will be used by the beneficial insects seeking a safe location as a shelter and thereby induce the beneficial insects to seek their food in the near vicinity. As these beneficial insects prefer attacking and consuming pests, the particular culture of plants remains free of attack by the pests.

The container may be provided in particular with a partly open bottom, a cylindrically or conically tapering side wall with several passage holes and a roof lid for ventilation and rain protection detachably mounted to the upper end. If desired a suspension system may also be provided, for instance in the form of a bail, which is held by a wire or the like passing through the container and fastened to the bottom. Preferably the wire passes through the bottom and connected to a support means at the lower side of the bottom. In this manner a very simple design is obtained, which nevertheless is quite functional, and the manufacturing costs are very low.

The filling may be cotton, rush, straw and the like, it should in any event be a material offering an environment preferred by the beneficial insects.

An embodiment of the invention is illustrated below in relation to the drawing; this single FIGURE shows a side view in partial section of a device for attracting beneficial insects.

In its basic design, the device consists a container 1 which in the embodiment shown is conical and comprises a side wall 2 made of a weatherproof material. The container 1 comprises a bottom 3 with side slots for the removal of filth, the bottom material also being weatherresistant. A lid 4 is provided at the top of container 1, for protecting against rain and is fixed in detachable manner to the container 1. Lid 4 in the example shown is of hemispherical design. A number of slip-through holes 5 for the beneficial insects being attracted are provided in the side wall 2 and in the lid 4.

The device shown furthermore is provided with a suspension means consisting of a wire bail 6 passing through the container 1 and bottom 3 and bent underneath bottom 3 into a support 8, so that the container can be suspended from the wire bail 6. However the container 1 also can be used without a suspension means. In that case it will be set on its bottom 3.

The container is filled in part with a natural substance filling 9. Such natural substances may be cotton, rush, straw or the like, but in any event they must be materials in which an environment preferred by the beneficial insects can develop.

I claim:

1. A device for controlling harmful insects by attracting beneficial insects, comprising:
   (a) a container having an open top and a closed bottom with a sidewall disposed therebetween;
   (b) a lid demountably engaging said top for covering said container for preventing ingress of rain into said container interior;
   (c) a plurality of beneficial insect openings in said sidewall comprising means for permitting said beneficial insects to freely enter and exit said container interior;
   (d) a plurality of beneficial insect openings in said lid comprising means for permitting said beneficial insects to freely enter and exit said container interior;
   (e) a non-poisonous natural beneficial insect attracting substance partially filling said container interior and providing an environment therein preferred by said beneficial insects for attracting said beneficial insects thereto; and,
   (f) said container positionable in a vegetated area populated with harmful insects whereby said beneficial insects are attracted to and seek shelter in said container and may freely exit said container for consuming said harmful insects and controlling said harmful insects thereby.

2. A device as defined in claim 1, wherein: said sidewall being generally conically tapered.

3. A device as defined in claim 1, further comprising: suspension means for hanging said device.

4. A device as defined in claim 3, wherein: said suspension means including a bale passing through said container and being fastened to said bottom.

5. A device as defined in claim 4, wherein: said bale passing through said bottom and forming a support means at the lower side of said bottom.

6. A device as defined in claim 1, wherein: said beneficial insect attracting substance including cotton.

7. A device as defined in claim 1, wherein: said beneficial insect attracting substance including rush.

8. A device as defined in claim 1 wherein: said beneficial insect attracting substance including straw.

9. A method for controlling harmful insect pests populating a vegetated area by attracting beneficial insects, comprising the steps of:
   (a) providing in said vegetated area a container having a plurality of openings therein for permitting free entry and exit of said beneficial insects;
   (b) providing in said container an environment preferred by said beneficial insects by partially filling said container with a non-poisonous natural beneficial insect attracting substance;
   (c) attracting said beneficial insects to said container;
   (d) permitting said beneficial insects to freely enter said container for seeking shelter therein; and
   (e) permitting said beneficial insects to freely exit said container for consuming said harmful insect pests for thereby controlling said harmful insect pests.

* * * * *